United States Patent [19]

Dai

[11] 4,328,361

[45] May 4, 1982

[54] NOVEL PROCESS

[75] Inventor: Shenghong A. Dai, Wallingford, Conn.

[73] Assignee: The Upjohn Company, Kalamazoo, Mich.

[21] Appl. No.: 225,459

[22] Filed: Jan. 16, 1981

[51] Int. Cl.³ .................. C07C 41/26; C07C 37/60
[52] U.S. Cl. .................. 560/130; 568/650; 568/771; 568/768; 568/763; 568/649; 568/774; 560/131; 560/144
[58] Field of Search ............ 568/650, 771, 768, 763, 568/649, 774; 560/131, 144, 130

[56] References Cited

U.S. PATENT DOCUMENTS 4,070,392  1/1978  Tresper et al. .................. 560/130
4,258,219  3/1981  Kato et al. .................. 568/771

*Primary Examiner*—Bernard Helfin
*Attorney, Agent, or Firm*—Denis A. Firth; John Kekich

[57] ABSTRACT

A process is disclosed for converting p-isopropenylphenol and derivatives thereof and, more particularly, oligomers of p-isopropenylphenol and derivatives thereof, to hydroquinone via monomeric intermediates [e.g. p-(2-haloisopropyl)phenol in the case of p-isopropenylphenol and oligomers thereof]. The process involves reacting the starting materials with a hydrogen halide (e.g. gaseous hydrogen chloride) in the presence of an organic solvent and subjecting the product so obtained to oxidation with hydrogen peroxide or an organic hydroperoxide.

18 Claims, No Drawings

NOVEL PROCESS

BACKGROUND OF THE INVENTION

1. Field of the Invention

This invention relates to a process for depolymerizing oligomers of p-(α-methylene-alkyl)phenols and is more particularly concerned with a process for converting said oligomers and the corresponding monomers to hydroquinone and related compounds.

2. Description of the Prior Art

Attention has recently been focused on the preparation of p-isopropenylphenol and the utilization of this compound in a variety of ways. For example, U.S. Pat. No. 4,207,265 describes the oxidation of p-isopropenylphenol to hydroquinone in high yield and also discloses a semi-continuous process in which phenol and acetone are condensed to form Bisphenol A, the latter is subjected to alkaline cleavage to give a mixture of phenol and p-isopropenylphenol, which latter is oxidized to hydroquinone and acetone and the recovered phenol and acetone are re-used in the synthesis of further Bisphenol A.

U.S. Pat. No. 4,054,611 describes a method of preparing p-isopropenylphenol in high yield in the form of a stable solution by condensing the vapor of p-isopropenylphenol in a solvent such as an alcohol as it is formed by thermal decomposition of Bisphenol A. This same reference refers to the problem of handling p-isopropenylphenol in solid, isolated form because of its tendency to polymerize to form a mixture of oligomers even at room temperature. It is shown that any oligomers so formed can be decomposed by heating at temperatures of 150° C. to 260° C. and collecting the monomer so produced by passing the vapors into a solvent such as alcohol.

German Application No. 2,508,512 describes the cracking of oligomers of p-isopropenylphenol by heating at 60° to 300° C. over an acid clay catalyst.

We have now found that it is possible to recover useful products, i.e. hydroquinone and derivatives thereof, from the oligomers of p-isopropenylphenol and related p-(α-methylenealkyl)phenols, as well as the alkyl ethers and acylated derivatives thereof, by a relatively simple procedure which does not involve the use of elevated temperatures or any form of thermal cracking.

SUMMARY OF THE INVENTION

The invention comprises (a) a process for reacting a compound having the formula

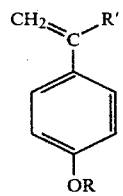

(I)

and oligomers thereof wherein R is selected from the class consisting of hydrogen, lower-alkyl and aryl and R' represents lower-alkyl, with at least a stoichiometric amount of a hydrogen halide in the presence of an inert organic solvent to form a monomeric halide of the formula

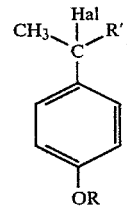

(II)

wherein R and R' have the significance above defined and Hal represents halogen;

(b) a process for reacting the compound (II), in solution in an inert organic solvent, with a peroxide selected from the class consisting of hydrogen peroxide and organic hydroperoxides to obtain the corresponding phenol having the formula:

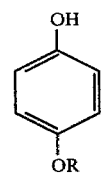

(III)

wherein R has the significance hereinbefore defined; and (c) a two step process which comprises converting Compound (I) and oligomers thereof to Compound (III) by carrying out processes (a) and (b) above in sequence.

The term "lower-alkyl" means alkyl having from 1 to 8 carbon atoms, inclusive, such as methyl, ethyl, propyl, butyl, pentyl, hexyl, heptyl, octyl and isomeric forms thereof. The term "acyl" means the acyl radical corresponding to a hydrocarbon carboxylic acid containing from 1 to 12 carbon atoms, inclusive, such as formic, acetic, propionic, butyric, isobutyric, valeric, trimethylacetic, hexanoic, heptanoic, octanoic, cyclopentylacetic, benzoic, ethylbenzoic, 2,4,6-trimethylbenzoic, α-naphthoic, phenylacetic, phenylpropionic acids and the like.

The term "halogen" is inclusive of chlorine, bromine and iodine.

The term "oligomers" means the dimers, trimers and higher polymers of the compounds of formula (I). The oligomers generally occur in the form of mixtures in which the dimers and trimers predominate. Illustrative of the various dimers and trimers derived from the compounds of formula (I) are:

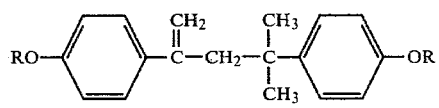

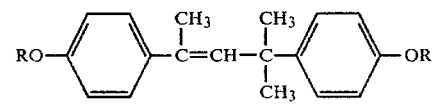

-continued

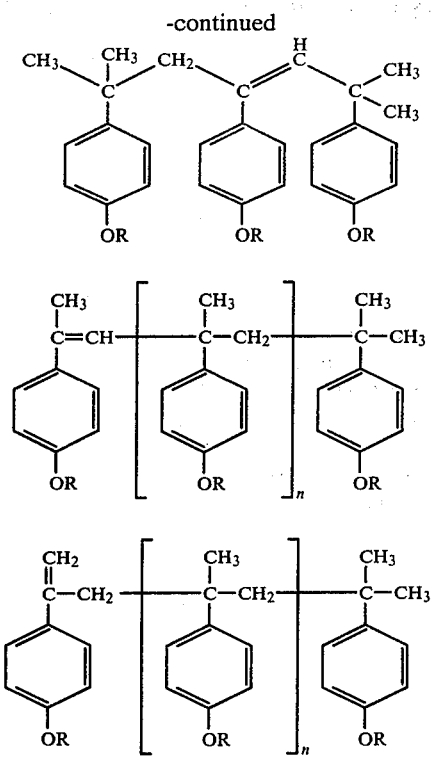

wherein R is above defined and n in both instances is an integer of at least 1. As will be obvious to one skilled in the art many of the above compounds can exist in stereoisomeric form but no attempt has been made to illustrate the individual isomers.

The term "inert organic solvent" is used throughout the specification and claims in its conventionally accepted sense, namely, as designating an organic solvent which does not enter into reaction with any of the reactants or interfere in any way with the desired course of the reaction. Illustrative of inert organic solvents are aromatic hydrocarbons such as benzene, toluene, xylene and the like; halogenated hydrocarbons such as methylene chloride, carbon tetrachloride, chloroform, ethylene dichloride, chlorobenzene, and the like; nitrobenzene; anisole; and dipolar aprotic solvents such as dimethyl sulfoxide, diethyl sulfoxide, diisobutyl sulfoxide, N,N-dimethylformamide, N,N-dimethylacetamide, tetramethylsulfone, 1-methylpyrrolidone, acetonitrile, chloroform, hexamethylphosphoramide and the like. Mixtures of two or more inert organic solvents can be employed if desired.

DETAILED DESCRIPTION OF THE INVENTION

In carrying out the step (a) in accordance with the invention the compound (I), or the oligomers thereof, or a mixture of (I) and its oligomers, is contacted with the appropriate hydrogen halide in the presence of an inert organic solvent. Advantageously the compound (I) and or the oligomers are dissolved or suspended in the solvent and the hydrogen halide is introduced into the solution or suspension in the form of a stream of gas. It is preferable to carry out the reaction in the substantial absence of moisture to minimize the possibility of decomposing the desired product (II) which latter tends to eliminate halogen readily in the presence of water. The reaction is carried out conveniently at ambient temperatures, i.e. of the order of 20° C. although lower (down to about −20° C.) or higher (up to about 50° C.) temperatures can be employed if desired.

The progress of the reaction can be followed utilizing routine analytical procedures such as nuclear magnetic resonance spectral analysis which enables one to check for disappearance of signals corresponding to the side-chain double bond and those corresponding to the appearance of absorptions of the new methyl group. When the reaction is judged complete using such techniques it is found that the oligomers, if present in the starting material, as well as the compound (I) have been converted in substantially quantitative yield to the corresponding halo compound (II). The amount of hydrogen halide which has been utilized to achieve this result is generally at least stoichiometric, i.e. 1 mole per mole in the case of the monomer, 2 moles per mole in the case of the dimer, and so on. Usually an excess over the stoichiometric amount is employed.

The product obtained by the above process is in the form of a solution of the compound (II) in the inert organic solvent and this solution is reasonably stable on storage under normal ambient temperature conditions in the absence of moisture. However, attempts to isolate the compound (II) in pure form from the solution, for example, by distilling off the solvent, generally result in dehydrohalogenation to yield the starting compound (I) or oligomers thereof. Accordingly, the compound (I) is utilized in step (b) of the process of the invention in the form of the solution obtained in the above step, optionally, after purging any excess of hydrogen halide from the reaction product utilizing a purge stream of inert gas such as nitrogen. However, such purging is not necessary as a preliminary to the following reaction.

Step (b) is carried out by reacting the solution of compound (II) obtained from step (a) as described above with hydrogen peroxide or an organic hydroperoxide.

The order in which the reactants are brought together is not critical. However, it is usually convenient to add the oxidizing agent to the solution of compound (II) rather than vice versa. The reaction is advantageously carried out at temperatures in the range of about −20° C. to 50° C. and, preferably, at temperatures in the range of about −5° C. to about 15° C. The oxidizing agent is used in proportions of at least stoichiometric, i.e. one equivalent per mole of compound (II), and advantageously is used in slight excess over the stoichiometric amount.

The progress of the reaction can be followed by routine analytical techniques such as those discussed above. When the reaction is adjudged complete, any excess peroxide is separated for example by fractionation by addition of water and the desired compound (III) is isolated from the reaction product by routine procedures. For example, the organic solvent is removed by distillation and the residue (III) is purified, if desired, by recrystallization and like techniques.

The organic hydroperoxides which can be employed in the above reaction can be any of those known in the art. Illustrative of such hydrocarbyl hydroperoxides are the alkyl hydroperoxides wherein alkyl contains from 1 to 12 carbon atoms such as methyl, ethyl, propyl, butyl, pentyl, hexyl, heptyl, octyl, nonyl, decyl, undecyl, and dodecyl including isomeric forms thereof; alkenyl hydroperoxides wherein alkenyl is from 3 to 12 carbon atoms, inclusive, such as allyl, butenyl, pentenyl, hexenyl, heptenyl, octenyl, nonenyl, decenyl, undecenyl, dodecenyl, and the like including isomeric forms thereof; cycloalkyl hydroperoxides wherein cycloalkyl is from 4 to 8 carbon atoms, inclusive, such as cyclobutyl, cyclopentyl, cyclohexyl, cycloheptyl, and cyclooctyl; cycloalkenyl hydroperoxides wherein cycloalkenyl is from 4 to 8 carbon atoms, inclusive, such as cyclobutenyl, cyclopentenyl, cyclohexenyl, cycloheptenyl, cyclooctenyl, and isomeric forms thereof; and aralkyl hydroperoxides wherein aralkyl is from 7 to 13 carbon atoms, inclusive, including benzyl, cumyl ($\alpha,\alpha$-dimethylbenzyl), phenethyl, $\alpha,\alpha$-diethylbenzyl, benzhydryl, $\alpha$-naphthylmethyl and the like.

Preferably, the hydrocarbyl hydroperoxides which are employed in the process of the invention are those in which the peroxy group is attached to a tertiary carbon atom and more particularly those hydroperoxides having the structure:

$$R_2-\underset{\underset{R_3}{|}}{\overset{\overset{R_1}{|}}{C}}-O-O-H$$

wherein $R_1$, $R_2$ and $R_3$ taken individually each represent alkyl as hereinbefore defined or aryl from 6 to 12 carbon atoms, inclusive and $R_1$ and $R_2$ taken together with the C atom to which they are attached represent cycloalkyl as hereinbefore defined. Illustrative of aryl are phenyl, tolyl, xylyl, biphenylyl, naphthyl, and the like.

Illustrative of tertiary hydroperoxides having the above formula are t-butyl hydroperoxide, phenylcyclohexane hydroperoxide, triphenylmethyl hydroperoxide, cumene hydroperoxide, o-, m-, and p-di-isopropylbenzene hydroperoxides, 1,3,5-triisopropylbenzene hydroperoxide, 1-methylcyclohexane hydroperoxide and the like.

The above reaction of step (b) is illustrated schematically as follows:

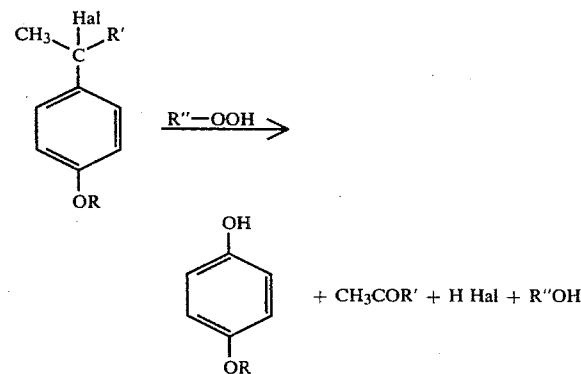

wherein R, R' and Hal have the significance defined above and R" is the hydrocarbyl residue of the hydroperoxide.

It will be seen that the processes of the invention represent a novel process for converting the compounds (I) via the intermediate (II) to yield hydroquinone or a monoalkyl ether or monoacyl derivative thereof. More particularly the processes of the invention provide a means of converting oligomers of the compounds (I) to monomeric compounds (II) and thence to yield hydroquinone or derivatives. This latter finding represents a valuable supplement to a process such as that described in the aforesaid U.S. Pat. No. 4,207,265 wherein hydroquinone is being prepared from p-isopropenylphenol and wherein some of the latter, which is being prepared by cleavage of Bisphenol A, is otherwise lost due to formation of oligomers in the cleavage or isolation process.

The following preparations and examples describe the manner and process of making and using the invention and set forth the best mode contemplated by the inventors of carrying out the invention but are not to be construed as limiting.

Preparation 1

A mixture of 69 g. (0.3 mole) of Bisphenol A and 0.08 g. of sodium hydroxide was heated under reduced pressure (circa 18 mm. of mercury) and a total of 64.7 g. of material distilled out of the mixture at a bath temperature of 20° C. (initial) to 280° C. (final). An aliquot of the distillate was analyzed by high pressure liquid chromatography and found to be a mixture of phenol and p-isopropenylphenol in a combined yield of 95% w/w. The distillate was then distilled at circa 18 mm. of mercury to remove the phenol (27 g.; 94 percent yield). The residual oil (37 g.) was found by high pressure liquid chromatography to be a mixture of p-isopropenylphenol (12% w/w), the dimer of p-isopropenylphenol (84% w/w), and Bisphenol A (4% w/w).

This residual oil was subjected to a second pyrolysis by heating in the presence of 0.08 g. of sodium hydroxide under reduced pressure (circa 18 mm. of mercury) under the same temperature conditions as described above. The distillate (36.1 g.; waxy solid) was found by gas liquid chromatography to contain p-isopropenylphenol (92% w/w), phenol (7% w/w) and a trace of the dimer of p-isopropenylphenol. The product was dissolved in 100 ml. of ether and the solution added with stirring to 600 ml. of water. A rapid stream of nitrogen was passed through the stirred mixture to evaporate the ether and the white precipitate which had separated was isolated by filtration. There was thus obtained 31.5 g. of p-isopropenylphenol having a melting point of 75° to 80° C. The product was recrystallized from ethylene dichloride to raise the melting point to 83°–85° C.

Preparation 2

The pyrolysis of Bisphenol A described in Preparation 1 was repeated and the residual oil, remaining after removal of phenol from the initial distillate, was added to 400 ml. of hot chlorobenzene and the resulting mixture was heated until clear and then cooled to circa 20° C. A trace of hydrogen chloride gas was bubbled into the cold solution and the latter was stirred for 30 minutes before being allowed to stand for 2 days at ambient temperature (circa 20° C.). The precipitate which separated was isolated by filtration, washed with chlorobenzene and dried at 70° C. under reduced pressure (25 mm of mercury). There was thus obtained 27.5 g. (68% yield) of the dimer of p-isopropenylphenol having a melting point of 125°–128° C. which was found by nuclear magnetic resonance spectroscopy to be substantially pure.

Preparation 3

The pyrolysis of Bisphenol A described in Preparation 1 was again repeated and the residual oil, remaining after removal of phenol from the initial distillate, was poured while still hot into 400 ml. of ethylene dichloride. A trace of hydrogen chloride gas was bubbled into the resulting solution (cooled to circa 20° C.) and the resulting mixture was stirred for 15 minutes and then allowed to stand for several days at ambient temperature (circa 20° C.). The solid which had separated was isolated by filtration and dried in vacuo at 80° C. There was thus obtained 18.6 g. of a crystalline solid having a melting point of 195° to 215° C. which was found by nuclear magnetic resonance spectral analysis to be a mixture of dimer and trimers of p-isopropenylphenol. A second crop (13.8 g.: melting point 205° to 216° C.) was obtained from the mother liquors by concentration.

Preparation 4

A solution of 42 g. (0.156 mole) of the dimer of p-isopropenylphenol (obtained by repeating the procedure of Preparation 2) in 200 ml. of methylene chloride was poured into 200 ml. of an aqueous solution containing 50 g. (1.25 mole) of sodium hydroxide and 0.7 g. of benzyltrimethylammonium chloride. To the resulting mixture was added dropwise, with vigorous stirring, a total of 70 g. (0.55 mole) of dimethyl sulfate over a period of 30 minutes. The temperature of the reaction mixture was maintained at 20° C. by cooling when necessary throughout the addition. When the addition was complete, the mixture was stirred for a further 17 hours at room temperature. At the end of this time the organic layer was separated and the aqueous layer was extracted twice with methylene chloride (2×50 ml.). The combined extracts were washed with ammonium hydroxide solution and then with sodium chloride solution before being dried over anhydrous magnesium sulfate. The solvent was evaporated to leave 43.2 g. of a residual oil which was found by high pressure liquid chromatography to contain 80% w/w of the methyl ether of the starting dimer and 15% w/w of the methyl ether of p-isopropenylphenol, the remainder being the dimethyl ether of Bisphenol A. This mixture was employed without further treatment as the starting material in Example 5 below.

EXAMPLE 1

Gaseous hydrogen chloride was passed into 0.7 ml. of deuterated chloroform in a 5 ml. vial until the chloroform was saturated. To the resulting solution was added 0.13 g. of p-isopropenylphenol (prepared as described in Preparation 1 and previously washed with n-hexane to remove traces of polymer) and the mixture was shaken at ambient temperature (circa 20° C.) until complete solution was achieved. The nuclear magnetic resonance spectrum of the solution was examined and found to be consistent with total conversion of the starting p-isopropenylphenol to p-(2-chloroisopropyl)phenol in accordance with the following equation:

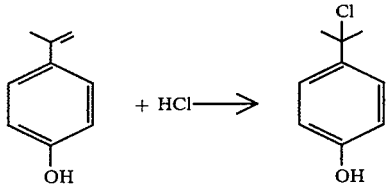

EXAMPLE 2

A mixture of 4.02 g. (0.03 mole) of the dimer of p-isopropenylphenol (prepared as described in Preparation 2) and 40 ml. of chloroform was stirred at ambient temperature (circa 20° C.) and gaseous hydrogen chloride was bubbled into the mixture until all the solid had dissolved. The formation of p-(2-chloroisopropyl)phenol was complete in 15 minutes. The resulting solution was then cooled to 10° C. and maintained thereat while a solution of 4.2 g. of tertiary-butyl hydroperoxide in 10 ml. of chloroform was added dropwise with stirring. After the addition was complete, the mixture was stirred for a further 15 minutes before adding 0.6 g. of water slowly so as to keep the temperature below 15° C. When this addition was complete, the mixture was stirred for 45 minutes before being cooled to 0° C. and filtered. There was thus obtained 2.65 g. of hydroquinone having a melting point of 168°–171° C. A second crop (0.13 g.) was obtained by partial evaporation of the chloroform filtrate. Total yield of hydroquinone=2.78 g. (85 percent theoretical yield based on dimer).

EXAMPLE 3

A mixture of 4.02 g. (0.01 mole) of a mixture of the dimer and trimers of p-isopropenylphenol (prepared as described in Preparation 3) and 40 ml. of a mixture of equal parts of chloroform and acetonitrile was stirred at ambient temperature (circa 20° C.) and gaseous hydrogen chloride was bubbled into the mixture until all the solid had dissolved. The nuclear magnetic resonance spectrum of the resulting solution showed that no trimer remained and formation of p-(2-chloroisopropyl)phenol was substantially complete. The resulting solution was then cooled to 10° C. and maintained thereat while a solution of 3.6 g. of tertiary-butyl hydroperoxide in 10 ml. of acetonitrile was added dropwise with stirring. After the addition was complete, the mixture was stirred for a further 15 minutes before adding 0.54 g. of water slowly with cooling so as to keep the temperature below 15° C. When this addition was complete, the mixture was stirred for 45 minutes before being cooled to 0° C. and filtered. There was thus obtained 2.75 g. of hydroquinone which was found by high pressure liquid chromatography to be 90% w/w pure representing a yield of 75% based on starting trimer.

EXAMPLE 4

A mixture of 12 g. (0.09 mole) of p-isopropenylphenol (prepared as described in Preparation 1) and 12 g. (0.118 mole) of acetic anhydride was stirred at ambient temperature (circa 20° C.) while two drops of concentrated sulfuric acid were added. Stirring was continued until the exothermic reaction subsided and the reaction product was then poured into an excess of water. The organic material was extracted with a mixture of ether and n-hexane and the extract was dried over anhydrous sodium sulfate and evaporated to dryness. There was thus obtained 16.5 g. of acetylated product which was found by nuclear magnetic resonance spectral analysis to be a mixture of 20% w/w of p-isopropenyl-phenol acetate and 80% w/w of the dimer diacetate. The product was subjected to pyrolysis by adding 0.1 g. of p-toluenesulfonic acid and heating to a temperature of 200°–240° C. under reduced pressure (circa 18 mm. mercury) to yield a distillate which was found to be 13.44 g. (85% yield) of monomeric p-isopropenylphenol acetate. The latter was mixed with a small amount of chloroform and hydrogen chloride gas was bubbled into the mixture until saturated. There was thus obtained a solution of p-(2-chloroisopropyl)phenol acetate.

EXAMPLE 5

Gaseous hydrogen chloride was bubbled into a solution containing 3 g. of the dimethyl ether of the dimer of p-isopropenylphenol (prepared as described in Preparation 4) in 50 ml. of acetonitrile at room temperature (20° C.) until a clear solution was obtained. Nuclear magnetic resonance spectral analysis showed the product to be mainly p-(2-chloroisopropyl)phenol in acetonitrile solution. To the solution, cooled to 5° to 10° C., was added, dropwise with stirring, a solution of 2.2 g. of tertiary-butyl hydroperoxide in 20 ml. of acetonitrile. When the addition was complete, the mixture was stirred for a further 30 minutes at 20° C. before adding 0.5 g. of water. The resulting product was evaporated to remove solvent and the residue was dissolved in methylene chloride and washed with water. The organic layer was separated, washed with aqueous sodium bicarbonate solution, dried over anhydrous magnesium sulfate and evaporated to dryness. There was thus obtained 3.45 g. of an oil which solidified on standing and which was shown by high pressure liquid chromatography to contain 81% w/w of hydroquinone monomethyl ether. The crude product was extracted with n-hexane and the hexane extract was evaporated to dryness. There was thus obtained 2.10 g. of hydroquinone monomethyl ether having a melting point of 50° to 55° C.

I claim:

1. A process which comprises reacting a compound having the formula

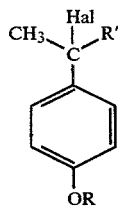

wherein Hal represents halogen, R is selected from the class consisting of hydrogen, lower-alkyl, and acyl and R' represents lower-alkyl, with an at least stoichiometric amount of a peroxide selected from the class consisting of hydrogen peroxide and organic hydroperoxides at a temperature of about −20° C. to about 50° C. to obtain the corresponding phenol having the formula

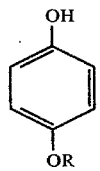

wherein R is as defined above.

2. The process of claim 1 wherein the starting material is p-(2-chloroisopropyl)phenol and there is thereby obtaned hydroquinone.

3. The process of claim 1 wherein said starting material has been obtained by reacting a compound selected from compounds of the formula

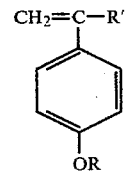

wherein R and R' have the meaning defined in claim 1, and oligomers thereof, with the appropriate hydrogen halide in the presence of an inert organic solvent and in the substantial absence of water at a temperature of about −20° C. to about 50° C.

4. The process of claim 1 wherein the starting material has been prepared by reacting a compound selected from the class consisting of p-isopropenylphenol and oligomers thereof with gaseous hydrogen chloride in the presence of an inert organic solvent and in the substantial absence of water at a temperature of about −20° C. to about 50° C.

5. The process of claim 4 wherein the inert organic solvent is acetonitrile.

6. The process of claim 4 wherein the inert organic solvent is chloroform.

7. A process for the preparation of a compound having the formula:

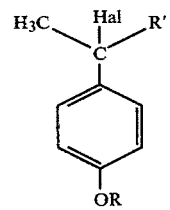

wherein Hal represents halogen, R is selected from the class consisting of hydrogen, lower-alkyl and acyl, and R' represents lower-alkyl, which process comprises reacting a compound selected from compounds of the formula:

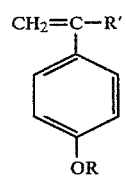

and oligomers thereof, wherein R and R' are as above defined, with hydrogen halide in the presence of an inert organic solvent and in the substantial absence of water at a temperature of about −20° C. to about 50° C.

8. The process of claim 7 wherein the hydrogen halide is hydrogen chloride and the inert organic solvent is acetonitrile.

9. The process of claim 7 wherein the hydrogen halide is hydrogen chloride and the inert organic solvent is chloroform.

10. A process for the conversion of a starting material selected from
    (a) compounds of the formula:

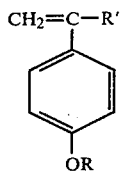

wherein R is selected from the class consisting of hydrogen, lower-alkyl and acyl and R' represents lower-alkyl;
(b) oligomers of said compounds; and
(c) mixtures of the said compounds and oligomers thereof;
to form a corresponding phenol of the formula:

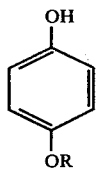

wherein R is as defined above; which process comprises reacting said starting material with at least a stoichiometric quantity of a hydrogen halide in the presence of an inert solvent and in the substantial absence of water at a temperature in the range of about −20° C. to about 50° C., and subjecting the reaction product so obtained to oxidation with a peroxide selected from the class consisting of hydrogen peroxide and organic hydroperoxides at a temperature in the range of about −20° C. to about 50° C. to obtain the said corresponding phenol.

11. The process of claim 10 wherein the starting material is a mixture of oligomers of p-isopropenylpheno whereby there is obtained hydroquinone.

12. The process of claim 10 wherein the starting material is a mixture of oligomers of p-isopropenylanisole whereby there is obtained hydroquinone monomethyl ether.

13. The process of claim 10 wherein the starting material is a mixture of oligomers of p-isopropenylphenol acetate whereby there is obtained hydroquinone monoacetate.

14. A process for conversion of a mixture of oligomers of p-isopropenylphenol to hydroquinone which process comprises reacting said oligomers with at least a stoichiometric amount of a hydrogen halide in the presence of an inert organic solvent and in the substantial absence of water at a temperature in the range of about −20° C. to about 50° C., and subjecting the intermediate p-(2-haloisopropyl)phenol so obtained to oxidation with a perioxide selected from the class consisting of hydrogen peroxide and organic hydroperoxides at a temperature in the range of about −20° C. to about 50° C., to obtain hydroquinone.

15. The process of claim 14 wherein said hydrogen halide is gaseous hydrogen chloride.

16. The process of claim 15 wherein the reaction with the hydrogen chloride is carried out in the presence of acetonitrile as the inert organic solvent.

17. The process of claim 15 wherein the reaction with the hydrogen chloride is carried out in the presence of chloroform as the inert organic solvent.

18. The process of claim 16 wherein the peroxide employed in the oxidation is tertiary-butyl hydroperoxide.

* * * * *

UNITED STATES PATENT OFFICE
CERTIFICATE OF CORRECTION

Patent No. 4,328,361      Dated May 4, 1982

Inventor(s) Shenghong A. Dai

It is certified that error appears in the above-identified patent and that said Letters Patent are hereby corrected as shown below:

Column 2, line 17 "perioxide" should read --peroxide--.
Column 4, line 29 "compound (I)" should read --compound (II)--.
Column 6, line 17 "20°C" should read --200°C--. Column 9, claim 2, line 65 "obtaned" should read --obtained--.

Column 12, claim 11, line 2 "p-isopropenylpheno" should read --p-isopropenylphenol--; column 12, line 20 "perioxide" should read --peroxide--.

Signed and Sealed this

*Fourteenth* Day of *September 1982*

[SEAL]

*Attest:*

*Attesting Officer*

GERALD J. MOSSINGHOFF
*Commissioner of Patents and Trademarks*